United States Patent [19]

Maul et al.

[11] Patent Number: 4,630,464

[45] Date of Patent: Dec. 23, 1986

[54] METHOD FOR THE CONTINUOUS SURVEILLANCE OF THE POISON CONTENT OF EXHAUST GASES CONTAINING PARTICULATE MATTER

[75] Inventors: Sonja Maul, Straubenhardt; Erwin Büttner, Stutensee; Heiner Meichelböck, Eggenstein-Leopoldshafen; Albert Merz; Hubert Vogg, both of Karlsruhe, all of Fed. Rep. of Germany

[73] Assignee: Kernforschungszentrum Karlsruhe GmbH, Karlsruhe, Fed. Rep. of Germany

[21] Appl. No.: 743,482

[22] Filed: Jun. 11, 1985

[30] Foreign Application Priority Data

Jun. 14, 1984 [DE] Fed. Rep. of Germany ....... 3422062

[51] Int. Cl.⁴ ............................................. G01N 15/02
[52] U.S. Cl. ............................................................ 73/28
[58] Field of Search ........... 73/28, 23, 863.03, 863.12, 73/863.23, 863.83, 863.81, 863; 55/270

[56] References Cited

U.S. PATENT DOCUMENTS 3,668,825  6/1972  McIlvaine ..................... 73/28
4,154,088  5/1979  Werner ......................... 73/28
4,191,541  3/1980  Jenkins ..................... 73/863.12
4,509,727  4/1985  Davis et al. ................... 73/28

Primary Examiner—Stephen A. Kreitman

[57] ABSTRACT

In a method for the continuous surveillance of the poison content of exhaust gases containing particulate material such as exhaust gases of large furnaces or waste incinerators, a sampling stream is continuously drawn from the exhaust gas stream through a suction line at a rate which corresponds to the exhaust gas stream flow rate, the sampling gas stream is passed through a cyclone in which any coarse particulate material is removed from and collected in a storage container, whereupon the sampling gas stream is passed through fine filter units in which fine particles are removed, a partial gas stream drawn from the particle free sample gas is passed through washing columns in which poisonous gases are washed out of the gas and dissolved in the washing liquid and from an analysis of the coarse and fine particulate material and the washing liquid, a poison distribution standard is determined whereupon for a period of time only coarse particulate material is collected and the poison content of the exhaust gas is then determined therefrom on the basis of the poison distribution standard.

2 Claims, 1 Drawing Figure

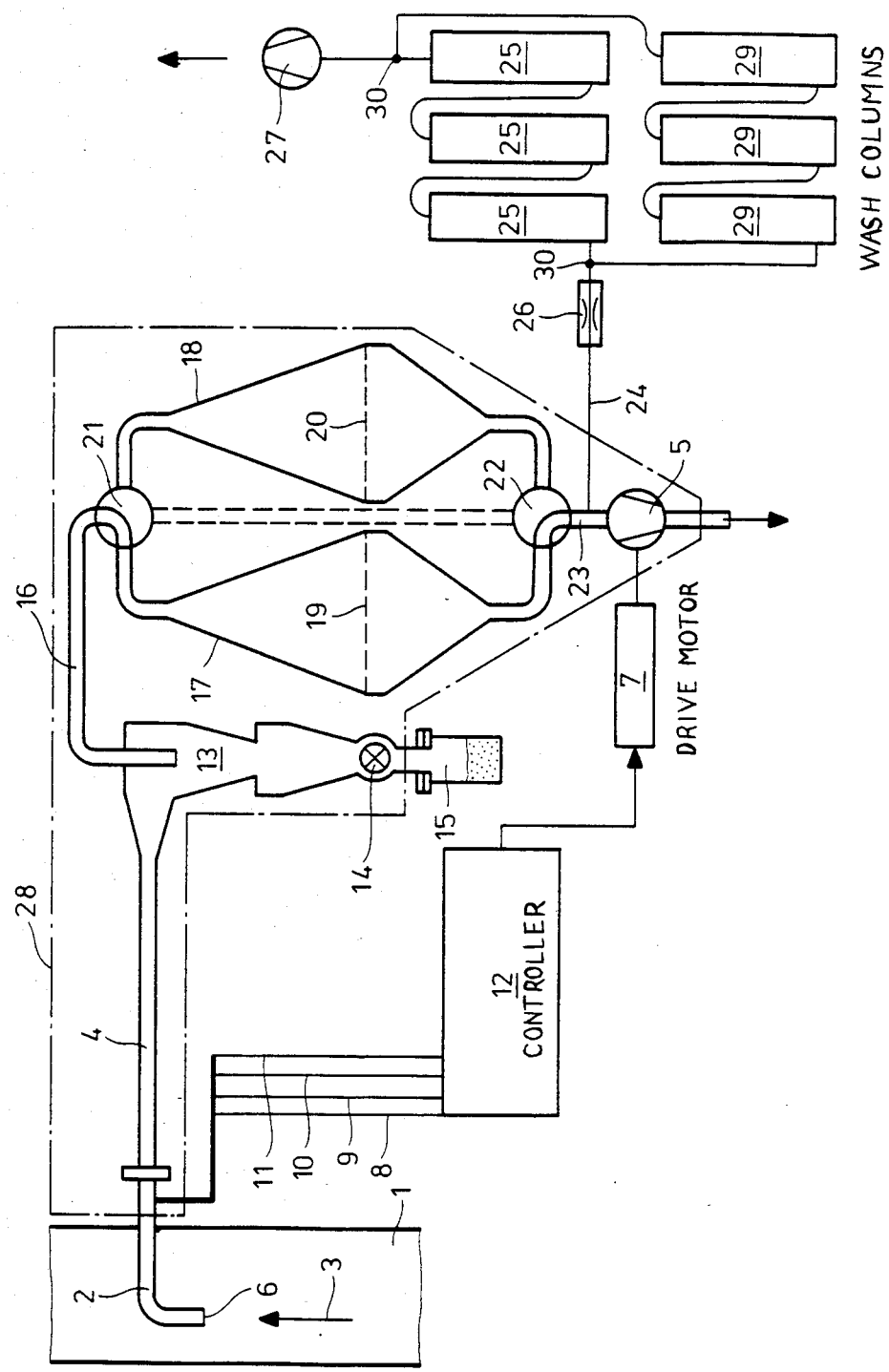

4,630,464

METHOD FOR THE CONTINUOUS SURVEILLANCE OF THE POISON CONTENT OF EXHAUST GASES CONTAINING PARTICULATE MATTER

BACKGROUND OF THE INVENTION

The invention relates to a method for a long-term determination and continuous serveillance of the poison content of exhaust gas streams containing particulate material such as exhaust gases of large furnaces or waste incinerators.

For the surveillance of exhaust gases, gas samples are generally taken from time to time for a short period which samples are tested but such momentary information is not well suitable for determining the tolerable long-term emissions and for the permanent surveillance of the exhaust gases.

Rather, reliable average daily, monthly and annual values are required which cover also all the poisonous emissions that may have occurred only intermittently.

It is the object of the present invention to provide a method for long-term determination and permanent surveillance of the poison content of exhaust gases charged with particulate material, that is, to provide a method permitting to take samples over a long period of time from such exhaust gas streams as waste incinerator plants, large furnaces or similar plants under isokinetic suction flow conditions, that is, at suction flows which are proportional to the amount of exhaust gas so that a complete and continuous count of the poison emissions such as dioxines, heavy metals etc., is warranted. The method must be suitable for continuous industrial surveillance of poison emissions. In order not to exceed, for example, the cadmium deposition value permitted in the vicinity of a waste incineration plat, it is absolutely necessary to obtain reliable average values of the cadmium emission of the incineration plant.

SUMMARY OF THE INVENTION

A reliable long-term surveillance of the poisonous content of exhaust gases containing particulate material such as those of large furnaces or waste incinerators is obtained by a method in which a sampling stream is continuously drawn from the exhaust gas stream at a rate corresponding to the flow rate of the exhaust gas stream and passed through a cyclone in which the coarse particulate material is removed and collected in a storage container. The sampling gas stream is then passed through fine-filter units in which fine particles are removed and a partial gas stream drawn from the particle-free sample gas stream is passed through washing columns in which poisonous gases are washed out of the gas and dissolved in the washing liquid for some period of time. From an analysis of the coarse and fine particulate material and the washing liquid, a poison distribution standard is then determined and, subsequently only the coarse particulate material is collected and the poison content of the exhaust gas is determined therefrom on the basis of the poison distribution standard.

It is a particular advantage of the method according to the invention that, for a continuous plant surveillance of poisonous emissions, particle separation may be limited to the first surveillance step, that is, to the gas cyclone particle operation, after the poisonous material distribution is established from previous standard determination which includes the subsequent filtering and washing or scrubbing steps. In this manner a complete determination of the amount of poisonous materials emitted by the exhaust gas becomes possible and by collecting and retaining the sampling materials the result may be checked, for example, by government agencies at any time.

SHORT DESCRIPTION OF THE DRAWINGS

The sole FIGURE shows schematically a measuring system for performing the method according to the invention.

DESCRIPTION OF THE PREFERRED EMBODIMENT

An exhaust gas duct 1 of a plant discharging poisonous substances includes a sampling device 2 through which a representative sample stream of the main gas stream 3 may be removed. Removal of the sample stream occurs in an isokinetic manner, that is, at a sample stream flow speed, which is the same as, or proportional to, that of the main gas stream, the necessary vacuum in the suction line 4 being provided by a suction blower 5. The flow speed of the sample gas stream at the port 6 of the sampling device is controlled by speed control of the HF drive motor 7 of the suction pump 5 by means of frequency control. Such isokinetic control of the suction at the port 6 of the sampling device 2 requires sensing of the following three pressure conditions: PG full pressure at 8; $pst_T$ static pressure of the sample stream at 9, $pst_H$ static pressure of the main gas stream at 10 and also of the temperature T (line 11) at the sampling device 2 in order to determine the momentary conditions at the port 6 of the sampling device 2. The pressures are transmitted by means of slots or channels in the walls of the sampling device. Utilizing the data so provided, a controller 12 determines and provides the frequency needed to operate the drive motor 7 at the speed necessary for the suction blower 5.

The path for the sample gas continues from the suction line 4 through a heated gas cyclone 13 for the continuous first stage separation of any coarse particulate material. The particulate materials separated from the sampling gas stream are continuously discharged from the cyclone 13, which has a relatively low interior pressure, into a storage container 15 by means of a rotating lock 14 or another type of discharge mechanism. The finely dispersed particulate material which cannot be separated and remains suspended in the sampling stream leaves the cyclone 13, that is, the first stage, through the conduit 16 and is conducted into filter housings 17 and 18 with fine pore filters 19, 20 on which the remaining fine particulate materials are retained. Switch-over valves 21 and 22 are provided to permit quasi-continuous operation by allowing switch-over between the filters 19 and 20 so as to permit a change of filter every 6 to 12 hours without interruption in the operation.

In flow direction, behind the filtering (second separation) stage, the discharge pipe 23 is provided with a diverted line 24 through which a small partial gas stream is continuously removed and, in a third stage, subjected to a scrubbing process by an acidic or alkaline liquid in one or more wash columns 25, 29 which are alternatively switchable into the line by a switch-over valve 30. In the wash process soluble poisonous gases are absorbed, that is, removed from the partial gas stream. The partial gas stream taken from the discharge line by means of a small pump 27 is maintained small by a flow throttling orifice 26 when compared to the sample gas stream which is about 50 m³/hr, so as not to cause disturbance of the isokinetic sampling gas speed control, that is, the control of the amounts of particulate materials removed from the main exhaust gas stream dependent on the varying exhaust gas flow conditions.

The separating equipment 13, 17 and 18 as well as the suction blower 5 and the suction line 4 are provided with heating means such as a heated enclosure 28 in order to avoid cooling of the equipment below the dew point of the gas within and thereby prevent condensation of any gaseous poison during separation of the solid particles from the gas stream. This is important inasmuch as it permits a distinct discrimination between poisonous solids and poisonous gases within the exhaust gas stream. After passing through the wash columns 25 or 29 the partial gas stream is discharged. Any poisonous gases washed from the partial gas stream are collected in the wash liquid and by determining their amount, the amount of poisonous gases in the exhaust gas is defined. In the same manner the particle amount and poisonous particle concentration in the storage container 15 permits the determination of the amount of poisonous particulate matter in the exhaust gas.

From the analysis of poisonous materials accumulated, a standard may then be determined which defines the volume relationship between the poisons in the coarse particulate material, the fine particulate material and the gaseous poison in the exhaust gas. After determination of the standard it is then sufficient only to collect, for example, the coarse particulate material and to determine therefrom the poison content of the exhaust gas on the basis of the poison distribution standard.

In this manner, accurate continuous surveillance is possible while full range samples have to be taken and analyzed only at given intervals for renewing the standard.

LIST OF REFERENCE NUMERALS

1 Exhaust gas duct
2 Sampling device
3 Main gas stream
4 Suction line
5 Suction blower
6 Sampling device port
7 Drive motor
8 Full pressure
9 Sample gas pressure
10 Main gas stream pressure
11 Temperature line
12 Controller
13 Gas cyclone
14 Rotating lock
15 Storage container
16 Conduit
17 Filter housing
18 Filter housing
19 Fine pore filter
20 Fine pore filter
21 Switch-over valve
22 Switch-over valve
23 Discharge pipe
24 Diverter line
25 Wash column
26 Throttling orifice
27 Pump
28 Heating means
29 Wash Column
30 Switch-ever valve

We claim:

1. A methed for the continuous surveillance of the poison content of exhaust gases containing particulate material such as the exhaust gases of large furnaces or waste incinerators wherein a sampling stream is continuously drawn from the exhaust gas stream through a suction line at a rate which corresponds to the exhaust gas stream flow rate and the particulate material is separated from the sampling gas stream under temperature-controlled conditions, said method being characterized by the following steps:
   (a) continuously separating from the sample gas stream in a gas cyclone as a first separation step any coarse particulate material,
   (b) continuously discharging the separated coarse particulate material from the gas cyclone, by means of a rotating lock, into a storage container,
   (c) continuously separating any fine particles suspended in the sample gas stream from the gas stream in alternatively connectable filter structure with exchangeable fine filters,
   (d) continuously drawing, with respect to the sample gas stream, a small partial gas stream from the sample gas stream downstream of said filter structure and conducting said partial gas stream through wash columns containing a liquid adapted to absorb any poisonous gases contained in said partial gas stream, and
   (e) determining, for a standard, the poison distribution in the exhaust gas stream from sample analysis of the material collected in the storage container, on the filters and in the wash liquid and, after establishment of the standard by the initial determination of the poison distribution in the exhaust gas stream, collecting only the coarse particulate material of the first separation step and determine therefrom the poison distribution in the exhaust gas on the basis of said standard.

2. A method according to claim 1, wherein the separating equipment, the suction blower and suction lines are heated so as to prevent condensation thereon.

* * * * *